United States Patent [19]

Hoffman

[11] Patent Number: 5,003,045

[45] Date of Patent: Mar. 26, 1991

[54] MODIFIED 7S LEGUME SEED STORAGE PROTEINS

[75] Inventor: Leslie M. Hoffman, Madison, Wis.

[73] Assignee: Lubrizol Genetics, Inc., Wickliffe, Ohio

[21] Appl. No.: 902,223

[22] Filed: Aug. 29, 1986

[51] Int. Cl.[5] .............................................. C07K 15/10
[52] U.S. Cl. .................................. 530/378; 530/350; 530/370; 435/69.1
[58] Field of Search ................... 435/68; 530/370, 378, 530/350

[56] References Cited

U.S. PATENT DOCUMENTS 4,670,388  6/1987  Rubin .............................. 435/172.3

OTHER PUBLICATIONS

Murai et al., 1983, Science 222: 476–482.
Slighton et al., 1983, Proc. Natl. Acad. Sci., U.S.A. 80: 1897–1901.
Higgins, T. J. V. 1984, Ann. Rev. Plant Physiol. 35: 191–221.
Beachy et al., 1985, The EMBO Journal 4: 3047–3053.
Pedersen et al., 1986, J. Biol. Chem. 261: 6279–6284.
Doyle et al., 1986, J. Biol. Chem. 261: 9228–9238.
Saalbach et al., 1988, Biochem. Physiol. Pflanzen, 183: 211–218.
Vasil, I. K., 1988, Bio/Technology 6: 397–402.
Fromm et al., 1985, Proc. Natl. Acad. Sci. 82: 5824–5828.
Hernalsteens et al., 1984, The EMBO J. 3(13): 3039–3041.
Hooykaas-Van Slogteren et al., 1984, Nature 311: 763–767.
Abstract (DBA Accession No. 86-02867), of Li et al., 1985, Plant Cell Rep. 4(6): 344–347.
Abstract (WPI accession No. 86-049581/08) of Patent No. EP 171679 to Hemphill et al., Feb. 19, 1986.
Abstract (DBA Accession No. 86-07396), of Prepy et al., 1986, Plant Cell Rep. 5(2): 124–126.
Selvin, S. B. 1987, Plant Molecular Biology 8: 355–359.
Horsch et al., 1985, Science 227: 1229–1231.
Klee et al., 1987, Ann. Rev. Plant Physiol. 38: 467–486.
Evans et al. (eds)., 1983, *Handbook of Cell Culture, vol. I,* Macmillan Publishers, pp. 18–20, 26, 27, 30–32.
Hoffman et al., 1988, Plant Molecular Biology, 11: 717–729.

*Primary Examiner*—Margaret Moskowitz
*Assistant Examiner*—Keith C. Furman
*Attorney, Agent, or Firm*—Greenlee and Associates

[57] ABSTRACT

The present invention discloses plant cells which contain modified 7S legume seed storage protein. Modification of 7S seed storage proteins which are expressible in plant cells and transformation of such genes into plant cells is also taught. Furthermore, methods and DNA molecules useful for producing plant cells containing modified 7S seed storage proteins are also disclosed. The invention is exemplified by insertion of an oligonucleotide encoding 15 amino acid residues, including 6 methionines, into a *Phaseolus vulgaris* phaseolin gene, thereby tripling its content of sulfur-containing amino acids.

12 Claims, 1 Drawing Sheet

MODIFIED 7S LEGUME SEED STORAGE PROTEINS

FIELD

The present invention is in the fields of genetic engineering and plant husbandry, and especially provides a means for producing modified 7S legume seed storage proteins in a plant by transforming a plant to contain a modified 7S legume seed storage protein gene. Also provided are plant-transforming prokaryotic plasmid vectors carrying such modified seed storage genes and plant cells transformed by such a vector.

BACKGROUND

Overview of Agrobacterium

Reviews of Agrobacterium-caused disease, plant transformation, genetic engineering, and gene expression include those by, or found in, Merlo DJ (1982) Adv. Plant Pathol. 1:139–178; Ream LW and Gordon MP (1982) Science 218:854–859; Bevan MW and Chilton M-D (1982) Ann. Rev. Genet. 16:357–384; Kahl G and Schell J (1982) *Molecular Biology of Plant Tumors*; Barton KA and Chilton M-D (1983) Meth. Enzymol. 101:527–539; Weissbach A and Weissbach H, eds. (1986) Meth. Enzymol. 118 (see especially Rogers SG et al., pp. 627–640); Depicker A et al. (1983) in *Genetic Engineering of Plants: an Agricultural Perspective*, eds: Kosuge T et al., pp. 143–176; Caplan A et al. (1983) Science 222:815–821; Hall TC et al., European Patent application 126,546; and Binns AN (1984) Oxford Surveys Plant Mol. Cell Biol. 1:130–160; Hall TC (1985) Oxford Surveys Plant Mol. Biol. 2:329–338; Hooykaas PJJ and Schilperoort RA (1985) Trends Biochem. Sci. 10:307–309; Thomas TL and Hall TC (1985) Bioassays 3:149–153; Puhler A, ed. (1983) *Molecular Genetics of the Bacteria-Plant Interaction*; and Schilperoort RA (1984) in *Efficiency in Plant Breeding* (Proc. 10th Congr. Eur. Assoc. Res. Plant Breeding), eds: Lange W et al., pp. 251–285.

Transformation of Plants by Agrobacterium

Plant cells can be transformed by Agrobacterium by several methods well known in the art. For a review of recent work, see Syono K (1984) Oxford Surveys Plant Mol. Cell Biol. 1:217–219. Inoculation of leaf disks is particularly advantageous (Horsch RB et al. (1985) Science 227:1229–1231).

The host range of crown gall pathogenesis may be influenced by T-DNA-encoded functions such as onc genes (Hoekema A et al. (1984) J. Bacteriol. 158:383–385; Hoekema A et al. (1984) EMBO J. 3:3043–3047; Buchholz WC and Thomasshow MF (1984) 160:327–332; Yanofsky M (1985) Mol. Gen. Genet. 201:237–246). Vir genes also affect host range (Yanofsky, supra).

Genes on the Transformation-Inducing Plasmids

The complete sequence of the T-DNA of an octopine-type plasmid found in ATCC 15955, pTi15955, has been reported (Barker RF et al. (1983) Plant Mol. Biol. 2:335–350) as has the TL region of pTiAch5 (Gielen J et al. (1984) EMBO J. 3:835–846). Published T-DNA genes do not contain introns. Sequences resembling canonical eukaryotic promoter elements and polyadenylation sites can be recognized.

The ocs gene encodes octopine synthase (lysopine dehydrogenase). Koncz C et al. (1983) EMBO J. 2:1597–1603 provides a functional analysis of ocs. Dhaese P et al. (1983) EMBO J. 2:419–426, reported the utilization of various polyadenylation sites by "transcript 7" (ORF3 of Barker R et al., supra) and ocs.

The nos gene encodes nopaline synthase (sequenced by Depicker A et al. (1982) J. Mol. Appl. Genet. 1:561–573). Shaw CH et al. (1984) Nucl. Acids Res. 12:7831–7846; and An G et al. (1986) Mol. Gen. Genet. 203:245–250, provide functional analyses of nos.

Ti and Ri plasmid genes outside of the T-DNA region include the vir genes, which when mutated result in an avirulent Ti plasmid. The vir genes function in trans, being capable of causing the transformation of plant cells with T-DNA of a different plasmid type and physically located on another plasmid. Such arrangements are known as binary systems and the T-DNA bearing plasmids are generally known as micro-Ti plasmids. Many binary systems are known to the art. T-DNA need not be on a plasmid to transform a plant cell; chromosomally located T-DNA is functional (Hoekema A et al. (1984) EMBO J. 3:2485–2490). Ti plasmid-determined characteristics have been reviewed by Merlo, supra (see especially Table II), and Ream and Gordon, supra.

Seed Storage Protein Expression

A gene encoding bean phaseolin has been transferred into and expressed in sunflower tumors. Transcription started and stopped at the correct positions, and introns were posttranscriptionally processed properly (Murai N et al. (1983) Science 222:476–482). The phaseolin gene was expressed at a high level in developing tobacco seeds (Sengupta-Gopalan C et al. (1985) Proc. Natl. Acad. Sci. USA 82:3320–3324). Similar results have been observed with soybean betaconglycinin which is about 60% homologous with the phaseolin gene (Beachy RN et al. (1985) EMBO J. 4:3047–3053). Some genes for the endosperm protein zein, from the monocot *Zea mays*, are transcribed in dicot cells, though translational products of these transcripts have not been detected (Matzke MA et al. (1984) EMBO J. 3:1525–1531, Goldsbrough et al. (1986) Mol. Gen. Genet. 202:374–381). Murai N et al. (1983) Science 222:476–482, reported fusion of the ocs promoter and its structural gene's 5'-end to a phaseolin structural gene, and expression thereof.

Legume Storage Proteins

A seed storage protein is a protein present in a seed having as its primary function the storage of amino acids for use by a seedling derived after germination of that seed to make other proteins. Legume storage proteins are reviewed by Derbyshire E et al. (1976) Phytochem. 15:3–24, and Millerd A (1975) Ann. Rev. Plant Physiol. 26:53–72. The 7S storage proteins are classified as such because of their sedimentation coefficient (about 7 svedbergs). Doyle JJ et al. (1986) J. Biol. Chem. 261:9228–9238, compare sequences of 7S storage proteins from *Phaseolus vulgaris* (phaseolin), *Glycine max* (beta-conglycinin), and *Pisum sativum* (vicilin and convicilin). They found that β-type phaseolin and the α' subunit of β-conglycinin have considerable homology at both the nucleotide and amino acid sequence levels (Doyle et al. (1986) J. Biol. Chem. 261:9228–9238). Doyle et al. compared the degree of apparent nucleotide divergence for 18 regions and found that the overall corrected divergence between these genes is about 41%. Protein sequences (Doyle et al., FIG. 2) shows that about 40% or more of those residues are either identical or have conservative substitutions (196 conserved or identical residues out of 509 residues compared).

SUMMARY OF THE INVENTION

It is well known that most herbivores cannot synthesize all twenty of the amino acids used to make proteins. These amino acids which must be supplied in the herbivore's diet, are referred to as "essential amino acids". For many species of mammals, the basic amino acids, i.e. lysine, and the sulfur-containing amino acids, e.g. methionine and cysteine, are essential. As cereal seed storage proteins are low in basic amino acids and legume storage proteins are low in sulfur-containing amino acids, mammalian diets often contain a mixture of legumes and grains so that the total amino acid complement consumed is balanced. The ability to express a 7S legume seed storage protein having relatively high levels of methionine in a plant can allow one to create a more nutritious plant having a better mix of amino acids. Therefore, it is an object of the present invention to increase the sulfur-containing amino acid content of a legume storage protein. Methods are provided for expression of these modified genes in plant cells. Furthermore, DNA molecules useful for this are provided. As exemplified herein, a 7S seed storage protein gene from *Phaseolus vulgaris*, phaseolin, has been modified to contain an insertion of methionine-encoding sequences of a *Zea mays* seed storage protein, zein. This modified gene has been expressed in seeds of *Nicotiana tabacum*. Phaseolin is a globulin (i.e., it is soluble in saline solutions), while zein is a prolamine (i.e., it is soluble in ethanolic solutions).

In particular, one can modify a 7S legume seed storage protein. A modification of the *Phaseolus vulgaris* 7S storage protein phaseolin is exemplified herein, but other 7S storage proteins, such as the *Glycine max* protein beta-conglycinin, could similarly be modified. The exemplified modification increases the particular phaseolin gene's content of sulfur-containing amino acids, in this case methionine, about three-fold. The modification can be one or more insertions or substitutions. DNA molecules having structural genes encoding such modified 7S legume seed storage protein can also be made. To express such a protein in a plant, one must have the structural gene combined with promoter and a polyadenylation site, the promoter, the structural gene, and the polyadenylation site being in such position and orientation with respect to each other that the structural gene is expressible in a plant cell under control of the promoter and the polyadenylation site. The promoter and the polyadenylation site are most conveniently derived from the same gene as the structural gene or from another 7S legume storage protein gene. The phaseolin and beta-conglycinin genes provide very useful promoters. A plant-expressible modified 7S seed storage protein gene can be transformed into a plant after it has been inserted into a T-DNA, which includes a T-DNA border repeat and a selectable or screenable marker (e.g. a neomycin phosphotransferase gene or an ocs gene). Also disclosed herein is a method for expressing a modified 7S legume seed storage protein in a plant cell by modifying a DNA sequence of a structural gene encoding a 7S legume seed storage protein, transforming a plant cell with the modified structural gene, the modified gene being expressible in a plant cell, and regenerating a plant descended from the transformed plant cell.

It is believed that before this invention there were no published reports of expression of an artificially modified 7S legume seed storage protein structural gene. Before the work presented herein was done, it was not known if, when expressed in a plant cell, a modified 7S legume seed storage globulin would be stable, if it would be glycosylated, if it would undergo proper post-translational processing, if it would be located in the proper cellular compartment, and if its polypeptide backbone would properly fold.

DETAILED DESCRIPTION OF THE INVENTION

Figure 1:
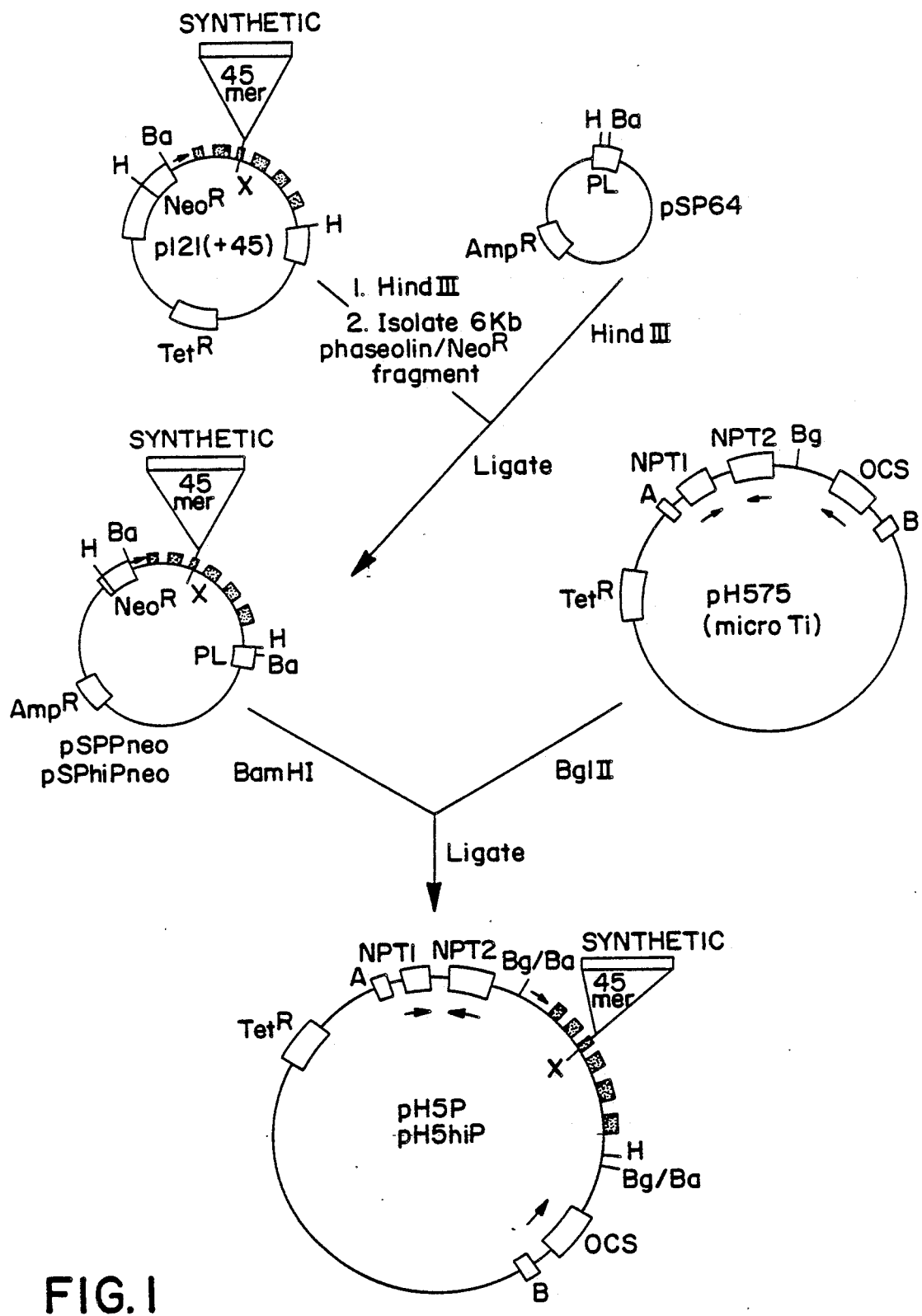
FIG. 1 diagrams, schematically and not necessarily to scale, construction of a micro-Ti plasmid carrying a plant-expressible phaseolin gene which has been modified to have an increased methionine content. Restriction sites have been abbreviated as follows: Ba, BamHI; Bg, BglII; H, HindIII; and X, XbaI. Other abbreviations include $Amp^R$ and $Tet^R$, respectively for bacterial resistance genes for ampicillin and tetracycline, NPT1 for a bacteria-expressible neomycin phosphotransferase I gene, NPT2 for a plant-expressible neomycin phosphotransferase II gene PL for a polylinker (a short stretch of DNA having numerous restriction sites), $Neo^R$ for a bacteria-expressible neomycin phosphotransferase II gene, OCS for a plant-expressible octopine synthase gene (ocs), and A and B for the octopine-type $T_L$-DNA A and B border repeats. Phaseolin exons are indicated by the solid-filled boxes. Open boxes indicate the $Tet^R$, $Amp^R$, PL (polylinker), borders A and B, NPT1, NPT2, $Neo^R$, and ocs. Additionally, for p121(+45), pSPPneo, and pSPhiPneo, open boxes can indicate the location of octopine-type $T_L$-DNA sequences that are not part of an indicated gene or border. Arrows inside a circle indicate the direction of transcription of the indicated gene while the arrow out of the circle next to the filled boxes indicates the location of the phaseolin promoter and its direction of transcription.

The following definitions are provided, in order to remove ambiguities to the intent or scope of their usage in the Specification and Claims.

7S Legume Seed Storage Protein: Refers to any protein having at least 20% homology to either the nucleic acid or protein sequence of either phaseolin or beta-conglycinin.

Modified Protein: Refers to having a different amino acid sequence than a naturally occurring protein.

Promoter: Refers to sequences at the 5'-end of a structural gene involved in initiation of transcription. A plant-expressible promoter is any promoter capable of driving transcription in at least one type of plant cell in at least one developmental stage. Eukaryotic promoter sequences are commonly recognized by the presence of DNA sequences homologous to the canonical form 5' . . . TATAA . . . 3' about 10–30 base pairs (bp) 5'-to the location of the 5'-end of the mRNA (cap site). About 30 bp 5'-to the TATAA, another promoter sequence is often found which is recognized by the presence of DNA sequences homologous to the canonical form 5' . . . CCAAT . . . 3'.

Transcript Terminator: Refers herein to any nucleic acid sequence capable of determining the position of the 3'-end of a transcript. The transcript terminator DNA segment may itself be a composite of segments derived from a plurality of sources, naturally occurring or synthetic, prokaryotic, or eukaryotic, and may be from a genomic DNA or an mRNA-derived cDNA (mRNA: messenger RNA). Transcript termination sites include polyadenylation sites and sites determining the 3'-end of ribosomal RNAs (rRNAs), transfer RNAs (tRNAs), and nonpolyadenylated mRNAs (e.g. histone mRNA: Krieg PA and Melton DA (1984) Nature 308:203–206).

A polyadenylation site is a nucleic acid sequence correlated with polyadenylation of mRNA in eukaryotes, i.e. after transcriptional termination polyadenylic acid "tails" are added to the 3'-end of mRNA precursors. Polyadenylation sites are commonly recognized by the presence of homology to the canonical form 5' . . . AATAAA . . . 3', although variations of distance 5' to the 3'-end of the transcript, partial "read-thru", and multiple tandem canonical sequences are not uncommon. DNA sequences between 20 and 35 bp downstream from the transcripts 3'-end seem to be necessary (McDevitt MA et al. (1984) Cell 37:993–999). It should be recognized that a canonical "polyadenylation site" may actually determine the location of the 3'-end of the mRNA and not polyadenylation per se (Proudfoot N (1984) Nature 307:412–413; Birnstiel ML et al. (1985) Cell 41:349–359).

Transcription Controlling Sequences: Refers to a promoter/transcript terminator site combination flanking a structural gene. The promoter and terminator DNA sequences flanking a particular foreign structural gene need not be derived from the same gene (e.g. pairing two different T-DNA transcripts) or the same taxonomic source (e.g. pairing sequences from T-DNA with sequences from non-T-DNA sources such as plants, animals, fungi, yeasts, eukaryotic viruses, bacteria, and synthetic sequences).

Translational Initiation Site: Refers herein to the 5'AUG3' translational start codon at the 5'-end of a structural gene, the nucleotide following the AUG, and the 3 nucleotides preceding the AUG (see Kozak M (1983) Microbiol. Rev. 47:1–45, and Kozak M (1984) Nucl. Acids Res. 12:857–872).

5'-Untranslated Sequence: Refers herein to the part of an mRNA between its 5'-end, or "cap site", and the translational start codon.

3'-Untranslated Sequence: Refers herein to the part of an mRNA between its translational stop codon and either its polyadenlylic acid segment or the 3'-end of a nonpolyadenylated mRNA.

Plant-Expressible Selectable or Screenable Marker: Refers herein to a genetic marker functional in a plant cell. A selectable marker (e.g. a kanamycin resistance gene) allows cells containing and expressing that marker to grow under conditions unfavorable to growth of cells not expressing that marker. A screenable marker (e.g. a beta-galactosidase gene) facilitates identification of cells which express that marker.

Plant-Expressible: Refers to the ability of a gene to be expressed in a plant cell. A gene is plant-expressible if a plant is capable of expressing it in at least one tissue or cell type in at least one developmental stage.

T-DNA: Refers in the art to the DNA sequence between and including two T-DNA border repeats capable of being transferred to a plant cell from a vir gene-containing Agrobacterium cell.

Transforming: Refers to the act of causing a cell to contain a nucleic acid molecule or sequence not originally part of that cell. Often, but not always, a transformation involves insertion of the transformed DNA into the cell's DNA.

Plant Tissue: Includes differentiated and undifferentiated tissues of plants including but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant Cell: As used herein includes plant cells in planta and plant cells and protoplasts in culture.

The following terms are well known in the art and are not specifically or specially defined herein: insertion, substitution, T-DNA border repeat, transcription under control of a promoter, and structural gene.

Production of a genetically modified plant cell expressing a modified 7S legume seed storage protein gene combines the specific teachings of the present disclosure with a variety of techniques and expedients known in the art. In most instances, alternative expedients exist for each stage of the overall process. The choice of expedients depends on variables such as the choice of the particular 7S seed storage protein gene, the particular modification, the exact location(s) of the modifications, the dicot species to be modified, the basic vector system for the introduction and stable maintenance of the promoter/structural gene combination, and the like, all of which present alternative process steps which those of ordinary skill are able to select and use to achieve a desired result. As novel means are developed for the stable insertion and transcription of foreign DNA in plant cells, those of ordinary skill in the art will be able to select among those alternate process steps to achieve a desired result. The fundamental aspects of the invention are the nature of the 7S seed storage protein and the nature of the modification thereof and the use of a gene encoding this storage protein to synthesize this modified protein in cells of plants transformed therewith. Other aspects include the means of insertion and expression of this modified gene in a plant genome. The remaining steps of the preferred embodiment for obtaining a genetically modified plant include inserting the combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene combination from the originally transformed strain into commercially acceptable cultivars, and monitoring expression in transformed plants.

A principal feature of the present invention in its preferred embodiment is the construction of a T-DNA derivative having an inserted modified gene under control of plant-expressible transcription controlling sequences, i.e., between a promoter and a transcript terminator, as these terms have been defined, supra. The structural gene must be inserted in correct position and orientation with respect to the promoter. Position relates to which side of the promoter the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of a structural gene insertion must be "downstream" from the promoter. Orientation refers to the directionality of the structural gene. That portion of a structural gene which encodes the amino terminus of a protein is termed the 5'-end of the structural gene, while that end which encodes amino acids near the carboxyl end of the protein is termed the 3'-end of the structural gene. Correct orientation of the structural gene is with the 5'-end thereof proximal to the promoter. Similarly to the promoter region, the transcript terminator must be located in correct position and orientation relative to the structural gene being proximal to the 3'-end of the structural gene. Differences in rates of gene expression or developmental control may be observed depending on the particular components, e.g. promoters, transcript terminators, flanking DNA sequences, or site of insertion into the transformed plant's genome. Storage protein accumulation may also be affected by storage protein mRNA stability, which can be greatly influenced by mRNA secondary structure, especially stem-loop structures. Different properties, including, but not limited to, such properties as stability, intracellular localization, posttranscriptional processing, and other functional properties of the expressed structural gene itself may be observed when promoter/structural gene/transcript terminator components are varied. All of these variations present numerous opportunities to manipulate and control the functional properties of the 7S seed storage protein, depending upon the desired physiological properties within the plant cell, plant tissue, and whole plant.

The fundamental principle of the present invention is that modified 7S legume seed storage globulins are capable of being made in plant cells that contain a plant-expressible modified 7S legume seed storage protein gene combination. The requirements for which DNA sequence segments are to be included in such a gene are best couched in functional terms. Transcript terminators, in particular polyadenylation sites, and promoters are understood in the art to be functional terms. However, the art understands a promoter to be that DNA segment capable of initiating transcription. Numerous promoters have been defined by methods such as deletion analysis. A promoter is the smallest continuous DNA segment that is necessary and sufficient to cause RNA polymerase to transcribe a flanking DNA segment. A promoter-bearing DNA segment may contain additional DNA sequences that are not necessary for transcription. Similarly, a polyadenylation site (or other transcript terminator) is functionally defined as the smallest continuous DNA segment that is necessary and sufficient to cause a transcript to become polyadenylated (or otherwise terminated). The functional requirements for a structural gene are also well understood. A structural gene must start with a translational initiation (start, AUG) site, end with a translational termination (stop) codon (UAA, UAG, or UGA) and have a integral number of triplet codons in-between, without an intervening stop codon.

The transcript of the modified 7S legume seed storage globulin gene may include heterologous sequences in addition to sequences encoding the modification. Inclusion of various heterologous sequences may affect mRNA stability, cellular localization of the mRNA, posttranscriptional processing, and the like. It is known to the art that RNA stability is affected by terminal structures such as 5'-capping and 3'-polyadenylation and by the extent of internal structure, i.e. intramolecular basepairing. Translational efficiency can similarly be affected by structures in the 5'-untranslated region, and by the exact sequence of the translational initiation site. An intron may be included in a mRNA, provided that, if the splice sites are derived from two different genes, the intron splice sites be compatible.

Combining of DNA segments, including coding, promoter, and transcript terminator sequences, to form a promoter/structural gene/terminator combination is accomplished by means known and understood by those of ordinary skill in the art of recombinant DNA technology. Choice of promoter depends on the developmental regulation desired. Use of developmentally regulated promoters for gene expression in plants is well known in the art. T-DNA or cauliflower mosaic virus promoters are advantageous as they are constitutive. The promoter of the gene for the small subunit of ribulose 1,5-bisphosphate carboxylase may be useful for expression in the green tissues of a plant transformed to contain a promoter/seed storage gene combination. The promoter of seed storage protein gene (e.g. phaseolin) can be used to express a monocot seed storage protein structural gene in plant seeds including seed of non-legumes (e.g. *Nicotiana tabacum*). In the preferred embodiments, the transcript terminator is a polyadenylation site. The plant gene source of the polyadenylation site is not crucial provided that the polyadenylation site, the promoter and the structural gene are compatible for transcription and posttranscriptional processing.

As will be apparent to those of ordinary skill in the art, the plant-expressible modified gene can be placed between any restriction sites convenient for removing the gene from the plasmid it is carried on and convenient for insertion into the plant transformation vector of choice. For example, location of the gene insertion site within T-DNA is not critical as long as the transfer function of sequences immediately surrounding the T-DNA borders are not disrupted, since in prior art studies these regions appear to be essential for insertion of the modified T-DNA into the plant genome. The gene/T-DNA combination is inserted into the plant transformation vector by standard techniques well known to those skilled in the art. The orientation of the modified gene with respect to the direction of transcription and translation of endogenous vector genes is not usually critical; generally, either of the two possible orientations is functional.

As is well known in the art, T-DNA of micro-Ti plasmids can be transferred from an Agrobacterium strain to a plant cell provided the Agrobacterium strain contains certain trans-acting genes whose function is to promote the transfer of T-DNA to a plant cell. Micro-Ti plasmids are advantageous in that they are small and relatively easy to manipulate directly, eliminating the need to transfer the gene to T-DNA from a shuttle vector by homologous recombination. After the modified gene has been inserted, the micro-Ti plasmid can easily be introduced directly into an Agrobacterium cell containing trans-acting vir genes, the vir genes usually being on a "helper plasmid", that promotes T-DNA transfer. Introduction into an Agrobacterium strain is conveniently accomplished either by transformation of the Agrobacterium strain or by conjugal transfer from a donor bacterial cell, the techniques for which are well known to those of ordinary skill. For purposes of introduction of novel DNA sequences into a plant genome, Ti plasmids, Ri plasmids, micro-Ti plasmids, and T-DNA integrated into chromosomes should be considered functionally equivalent.

T-DNA having a modified 7S seed storage protein gene can be transferred to plant cells by any technique known in the art. For example, this transfer is most conveniently accomplished by cocultivation of the Agrobacterium strain with plant cells or with plant tissues. Using these methods, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker or screenable marker incorporated into the T-DNA in addition to the gene combination. Examples of artificial markers are well known in the art. In addition, the T-DNA provides endogenous markers such as gene(s) controlling abnormal morphology of Ri-induced tumor roots and gene(s) that control resistance to toxic compounds such as amino acid analogs, such resistance being provided by an opine synthesizing enzyme (e.g. ocs). Screening methods well known to those skilled in the art include, but are not limited to, assays for opine production, specific hybridization to characteristic nucleic acid sequences (e.g. storage protein mRNA or T-DNA) or immunological assays for specific proteins (e.g. phaseolin or neomycin phosphotransferase II).

Although the preferred embodiments involve use of micro-Ti plasmids, other T-DNA-based vector systems known to the art may readily be substituted. Furthermore, though the preferred embodiment of this invention incorporates a T-DNA-based Agrobacterium-mediated system for incorporation of the modified 7S seed storage protein gene into the genome of the plant which is to be transformed, other means for transferring and incorporating the modified gene into a plant genome are also included within the scope of this invention. Other means for the stable incorporation of the modified gene into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, fusion with vector-containing liposomes or bacterial spheroplasts, microinjection, encapsidation in viral coat protein followed by an infection-like process, and direct uptake of DNA, possibly after induction of plasmalemma permeability by an electric pulse, a laser, or a chemical agent. Means for transient incorporation and/or expression are also included within the scope of this invention. Systems based on Agrobacterium cells and T-DNAs can be used to transform angiosperms, including dicots and monocots, by transfer of DNA from a bacterium to a plant cell; systems based on alternate vectors or means for vector delivery may be used to transform gymnosperms and angiosperms.

Regeneration of transformed cells and tissues is accomplished by resort to known techniques. An object of the regeneration step is to obtain a whole plant that grows and reproduces normally but which retains integrated T-DNA. The techniques of regeneration vary somewhat according to principles known in the art, and may depend upon the plant transformation vector and the species of the transformed plant. Regeneration of transformed tobacco plants, petunia plants, and plants of related species is well known to the art. As means for regeneration of other plant species are developed, the art will understand, without undue experimentation, how to adapt these newly discovered means for regeneration of plants from transformed plant cells and transformed plant tissues.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced gene may be readily transferred to the desired agronomic cultivar by techniques well known to those skilled in the arts of plant breeding and plant genetics. Sexual crosses of transformed plants with the agronomic cultivars yield initial hybrids. These hybrids can then be back-crossed with plants of the desired genetic background. Progeny are continuously screened and/or selected for the continued presence of the introduced gene, T-DNA, or for a new phenotype resulting from expression of the gene combination or other genes carried by the inserted DNA. In this manner, after a number of rounds of backcrossing and selection, plants can be produced having a genotype essentially identical to the agronomically desired parents with the addition of inserted DNA sequences.

EXAMPLES

The following Examples are presented for the purpose of illustrating specific embodiments within the scope of the present invention without limiting the scope, the scope being defined by the claims. Numerous variations will be readily apparent to those of ordinary skill in the art.

The Examples utilize many techniques well known and accessible to those skilled in the arts of molecular biology and manipulation of T-DNA and Agrobacterium; such methods are fully described in one or more of the cited references if not described in detail herein. All references cited in this Specification are hereby incorporated by reference. Enzymes are obtained from commercial sources and are used according to the vendors' recommendations and other variations known to the art. Reagents, buffers, and culture conditions are also known to those in the art. Reference works containing such standard techniques include the following: Wu R, ed. (1979) Meth. Enzymol. 63; Wu R et al., eds. (1983) Meth. Enzymol. 100 and 101; Grossman L and Moldave K, eds. (1980) Meth. Enzymol. 65; Weissbach A and Weissbach H, eds. (1986) Meth. Enzymol. 118 (see especially Rogers SG et al., pp. 627–640); Miller JH (1972) *Experiments in Molecular Genetics*; Davis R et al. (1980) *Advanced Bacterial Genetics*; Schleif RF and Wensink PC (1982) *Practical Methods in Molecular Biology*; Walker JM and Gaastra W, eds. (1983) *Techniques in Molecular Biology*; and (1983) Genet. Engin. 4:1–56, make useful comments on DNA manipulations.

Textual use of the name of a restriction endonuclease in isolation, e.g. "BclI", refers to use of that enzyme in an enzymatic digestion, except in a diagram where it can refer to the site of a sequence susceptible to action of that enzyme, e.g. a restriction site. In the text, restriction sites are indicated by the additional use of the word "site", e.g. "BclI site". The additional use of the word "fragment", e.g. "BclI fragment", indicates a linear double-stranded DNA molecule having ends generated by action of the named enzyme (e.g. a restriction fragment). A phrase such as "BclI/SmaI fragment" indicates that the restriction fragment was generated by the action of two different enzymes, here BclI and SmaI, the two ends resulting from the action of different enzymes.

Plasmids, and only plasmids, are prefaced with a "p", e.g., pTi15955 or pH400, and strain designations parenthetically indicate a plasmid harbored within, e.g., *A. tumefaciens* (pTi15955) or *E. coli* H802 (pH400). The following strains have been deposited:

| E. coli K802 (pCT29K-2) | NRRL B-18010 |
| A. tumefaciens (pTi15955) | ATCC 15955 |
| E. coli HB101 (p3.8) | NRRL B-15392 |

(ATCC: American Type Culture Collection, 12301 Parklawn Dr., Rockville, Md. 20852 USA; NRRL: ARS Patent Collection, Northern Regional Research Center, 1815 N. University St., Peoria, Ill. 61614 USA.) Other plasmids and strains are widely available and accessible to those in the art.

EXAMPLE 1

Construction of a micro-Ti plasmid, pH575

*E. coli* K802 (pCT29K-2), which has been deposited as NRRL B-18010, was disclosed by Sutton DW et al., U.S. patent application Ser. No. 788,984, which is hereby incorporated by reference. The T-DNA of pCT29K-2 can be represented as follows:
borderA . . . bacteria-selectable NPT1 . . . unique BglII site . . . plant-selectable NPT2 . . . 5'-end of tml . . . ocs . . . border B.
Except for NPT1 (NPT1 is neomycin phosphotransferase I, NPT2 is neomycin phosphotransferase II), all of these genes are transcribed in the same direction. This T-DNA can be removed from pCT29K-2 on a 9.52 kbp Hind III fragment.

The micro-T-DNA-carrying 9.52 kbp (kilobase pair) HindIII fragment of pCT29K-2 was mixed with and ligated to HindIII-linearized, dephosphorylated pTJS75 DNA (see Klee HJ et al. (1985) Biotechnol. 3:637–642). Restriction mapping of *E. coli* transformants resistant both to kanamycin and to tetracycline resulted in identification of a colony harboring a plasmid designated pH575 (FIG. 1).

EXAMPLE 2

Preparation of a phaseolin gene p121 (Murai N et al. (1983) Science 222:476–482) has the pTi15955 BamHI fragment spanning positions 9,062 and 13,774 (T-DNA positions are as reckoned by Barker RF et al. (1983) Plant Mol. Biol. 2:335–350) inserted into the BglII site of pRK290 (Ditta G et al. (1980) Proc. Natl. Acad. Sci. USA 77:7347–7351). The T-DNA position 11,207 SmaI site had been converted to a HindIII site and a 6.8 kbp HindIII fragment having a phaseolin gene on a 3.8 kbp BamHI/BglII segment carried by p3.8 (AG-PVPh3.8 of Slightom JL et al. (1983) Proc. Natl. Acad. Sci. USA 80:1897–1901), a Tn5kanamycin resistance gene (kan), and some pBR322 sequences; both the phaseolin and kan genes are oriented parallel to the T-DNA tml gene. p121 is described in greater detail by Hall TC et al., European patent application Ser. No. 84302533.9 wherein it is designated p499/6/7. *E. coli* K802 (p499/6/7) has been deposited as NRRL-15384.

EXAMPLE 3

Insertion of methionine codons into phaseolin gene p121 has a single XbaI site which is within the third phaseolin exon at about position 805 as reckoned by Slightom et al., supra. XbaI-linearized, p121 DNA was mixed with and ligated to a phosphorylated synthetic oligonucleotide having the following duplex structure:

5'CTAGACCAGATGAGAATGATGGACCAGATGAGGATGATGGACGTT3'
3'TGGTCTACTCTTACTACCTGGTCTACTCCTACTACCTGCAAGATC5'

This oligonucleotide encodes 15 amino acids, and has a composition of $Arg_2Asp_3Gln_2LeuMet_6Val$, basically representing a duplication of a 15 kD zein sequence encoded by DNA resides 271–291, reckoned as described by Pedersen K et al. (1986) J. Biol. Chem. 261:6279–6284, inserted into the phaseolin structural gene. This particular 15 kD zein peptide was chosen for its high content of methionine and its alpha-helical structure as predicted by the well known algorithm of Chou and Fasman. This oligonucleotide also contained a FokI restriction site useful for detecting and determining the orientation of the insert, and six methionine codons. When inserted into the phaseolin gene, this oligonucleotide triples the quantity of methionine encoded thereby. (The mature phaseolin polypeptide encoded by the unmodified gene contains three methionine residues, the two methionine residues at the amino terminus being removed by posttranslational processing of the signal peptide.) After ligation the modified phaseolin gene has the following structure:

```
... phaseol 808      271    zein    288 271      zein       291 805   phaseolin ...
... HisIleLeuAspGlnMetArgMetMetAspGlnMetArgMetMetAspValLeuGluAla ...
5' ... CATATTCTAGACCAGATGAGAATGATGGACCAGATGAGGATGATGGACGTTCTAGAGGCC ... 3'
3' ... GTATAAGATCTGGTCTACTCTTACTACCTGGTCTACTCCTACTACCTGCAAGATCTCCGG ... 5'
        XbaI                                    FokI              XbaI
```

The uppermost portion of the above representation indicates the protein from which the sequence below the line was derived, with the numbers on the ends of the lines indicating the coordinate of the end of the segment as reckoned by Pedersen et al. for zein and Slightom et al. for phaseolin. Note that duplication of the XbaI site lead to duplication of a phaseolin leucine residue encoded thereby, and that the Asp-Gln doublet in the middle of the insertion is duplicated at the 5'-end of the insert. The ligation mixture was transformed into *E. coli* MC1061 and selected for resistance to tetracycline. Colonies containing the oligonucleotide were identified by hybridization with [32P]-labeled oligonucleotide. A colony was identified by restriction mapping of DNA isolated therefrom which harbored a plasmid, designated p121(+45) (FIG. 1), having the insertion in the orientation so that it encoded an amino acid sequence as indicated above.

EXAMPLE 4

Placement of phaseolin gene between Bam HI sites p121(+45) DNA was digested with HindIII and a 6 kbp fragment carrying the phaseolin gene/kan combination was electrophoretically isolated. This 6 kbp fragment was mixed with and ligated to HindIII-linearized pSP64 (FIG. 1) DNA (Melton DA et al. (1984) Nucl. Acids. Res. 12:7035-7056). After transformation into *E. coli* MC1061, DNAs isolated from transformants resistant to ampicillin and tetracycline were characterized by restriction mapping. A colony was identified which harbored a plasmid designated pSPhiPneo (FIG. 1) having the modified phaseolin on a 4.1 kbp BamHI fragment in pSP64.

The above operations were also done with p121 substituting for p121(+45) as a starting material. This resulted in identification of a colony which harbored a plasmid designated pSPPneo (FIG. 1) lacking the 45 bp (base pair) insertion in the phaseolin gene but was otherwise identical to pSPhiPneo.

EXAMPLE 5

Insertion of phaseolin gene into a micro-Ti

BamHI-digested pSPhiPneo DNA was mixed with and ligated to BglII-linearized pH575 DNA. After transformation into *E. coli*, DNAs isolated from tetracycline-resistant transformants were characterized by restriction analysis. A colony was identified which harbored a plasmid, designated pH5hiP (FIG. 1), having the modified phaseolin gene inserted into the pH575 T-DNA.

The above operations were also done with pSPPneo substituting for pSPhiPneo as a starting material. This resulted in identification of a colony which harbored a plasmid designated pH5P (FIG. 1). pH5P lacked the 45 bp insertion in the phaseolin gene but was otherwise identical to pH5hiP. pH5P served as a wild-type phaseolin control for the pH5hiP mutant.

EXAMPLE 6

An alternative manipulation of phaseolin

A somewhat simpler construction is also possible. p3.8 is opened at its sole XbaI site which is located within the phaseolin gene. The 45 bp insert is then ligated into the phaseolin gene. This modified gene can be removed on a 3.8 kbp BamHI/BglII fragment and be inserted into the BglII site of pH575. The resulting high methionine phaseolin gene-carrying micro-Ti plasmid is virtually identical with pH5hiP, differing only in some sequences 5'-from the phaseolin gene. p3.8 can also be used to make a control plasmid virtually identical to pH5P.

EXAMPLE 7

Plant transformation pH5hiP and pH5P were individually transferred into *A. tumefaciens* LBA4404 (Ooms G et al. (1981) Gene 14:33-50), a vir gene-harboring, micro-Ti-mobilizing strain, by the triparental mating technique (Ruvkun GB and Ausubel FM (1981) Nature 289:85-88), which is well known in the art. Tobacco leaf tissue was obtained from 4- or 5-week old *Nicotiana tabacum* var. Xanthi$^{NC}$ plants grown in a greenhouse. Inoculation was by a modification of the method Horsch RB et al. (1985) Science 227:1229-1231. Inocula were prepared by placing two loopfuls of agrobacteria in 10 ml of L-broth. After suspension by forceful pipetting with a Pasteur pipet, inocula could be used immediately. Leaves were excised and midribs were removed; cutting surfaces were wetted with L-broth to help keep the leaves wet. Leaf pieces were about 2-4 mm wide and about 7-10 mm long. Leaf pieces were dipped in the inoculum for 5-10 min, though in some experiments, leaf pieces were just dipped into the inoculum or were infiltrated with the inoculum in a vacuum flask. Pieces were then blotted dry on sterile filter paper and placed upside down on feeder plates prepared from a Xanthi suspension culture. The feeder plates had a SMPi medium (SMPi: MX$^-$ supplemented with 0.1 mg/l p-chlorophenoxyacetic acid (pCPA) and 7.5 mg/l 6-(8,8-dimethylallylamino)purine (2iP); MX$^-$: 1.65 g/l NH$_4$NO$_3$, 1.9 g/l KNO$_3$, 440 mg/l CaCl$_2$·2H$_2$O, 370 mg/l MgSO$_4$·4H$_2$O, 170 mg/l KH$_2$PO$_4$, 0.83 mg/l KI, 6.2 mg/l H$_3$BO$_3$, 22.3 mg/l MnSO$_4$·4H$_2$O, 8.6 mg/l ZnSO$_4$·7H$_2$O, 0.25 mg/l Na$_2$MoO$_4$·2H$_2$O, 0.025 mg/l CuSo$_4$·5H$_2$O, 0.025 mg/l CoCl$_2$·6H$_2$O, 1 g/l inositol, 50 mg/l nicotinic acid, 50 mg/l pyroxidine·HCl, 50 mg/l thiamine·HCl, 30 g/l sucrose, pH 5.8, solidified with 8 g/l agar). Leaf pieces were removed from feeder plates after 4-6 days and placed on SMPi medium supplemented with 500 mg/l carbenicillin, 50 mg/l cloxacillin, and 100-300 mg/l kanamycin (200 mg/l optimum). The resulting shoots were excised and placed on MX$^-$ medium supplemented with 100-300 mg/l kanamycin (200 mg/l optimum).

EXAMPLE 8

Expression in plants

Regenerated tobacco plants descended from cells transformed by *A. tumefaciens* LBA4404 (pH5hiP) or *A. tumefaciens* LBA4404 (pH5P) were self-fertilized. The resulting can be germinated on MX$^-$ supplemented with 100-300 mg/l kanamycin (200 mg/l optimum) to select plants containing the nonmonocot promoter/-monocot seed storage protein structural gene-bearing T-DNA. Presence of the transformed T-DNA was confirmed by Southern blot analysis. Presence of mRNA encoding modified or unmodified phaseolin can be confirmed by Northern blot analysis. Presence of phaseolin protein in developing tobacco seeds was detected by SDS-polyacrylamide gel electrophoresis followed by transfer to membrane filters and immunological detection (western blots). Modified phaseolin was observed in seeds of plants transformed by pH5hiP. The phaseolin promoter is known to be able to express phaseolin in tobacco seeds at levels above about 0.05% total protein levels, often at a level of about 1% protein.

I claim:

1. A modified 7S legume seed storage protein produced by the process of inserting into a nucleotide sequence encoding a 7S legume seed storage polypeptide sequence a zein nucleotide sequence, and expressing said sequence to produce said modified protein whereby the insertion increases the protein's methionine amino acid content relative to the 7S legume seed storage protein as it exists in nature.

2. A protein produced by the process of claim 1, wherein the legume is of the genus Phaseolus.

3. A protein produced by the process of claim 1, wherein the legume is *Phaseolus vulgaris*.

4. A protein produced by the process of claim 2, wherein the storage protein is phaseolin.

5. A protein produced by the process of claim 4, wherein the phaseolin polypeptide is encoded by plasmid p3.8.

6. A protein produced by the process of claim 5, wherein the zein sequence is inserted into position 805 XbaI site within the plasmid p3.8 phaseolin structural gene.

7. A protein produced by the process of claim 1, wherein the legume is of the genus Glycine.

8. A protein produced by the process of claim 7, wherein the storage protein is beta-conglycinin.

9. A protein produced by the process of claim 1, wherein the insertion is a peptide about 15 amino acid residues long.

10. A protein produced by the process of claim 1, wherein the inserted peptide has a composition of about $Arg_2, Asp_3, Gln_2, Leu, Met_6, Val$.

11. A protein produced by the process of claim 1, wherein the inserted peptide has a sequence comprising AspGlnMetArgMetMetAspGlnMetArgMetMetAspValLeu.

12. A protein produced by the process of claim 11, wherein the protein is the protein encoded by plasmid pSPhiPneo.

* * * * *